United States Patent
Kamon et al.

(10) Patent No.: US 10,932,871 B2
(45) Date of Patent: Mar. 2, 2021

(54) SURGICAL ROBOT

(71) Applicant: KAWASAKI JUKOGYO KABUSHIKI KAISHA, Kobe (JP)

(72) Inventors: Masayuki Kamon, Akashi (JP); Kenji Noguchi, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 0 days.

(21) Appl. No.: 14/655,443

(22) PCT Filed: Dec. 25, 2013

(86) PCT No.: PCT/JP2013/084647
§ 371 (c)(1),
(2) Date: Jun. 25, 2015

(87) PCT Pub. No.: WO2014/104088
PCT Pub. Date: Jul. 3, 2014

(65) Prior Publication Data
US 2015/0351864 A1    Dec. 10, 2015

(30) Foreign Application Priority Data
Dec. 25, 2012 (JP) .................................. 2012-281613

(51) Int. Cl.
*A61B 17/00* (2006.01)
*A61B 34/35* (2016.01)
(Continued)

(52) U.S. Cl.
CPC .............. *A61B 34/35* (2016.02); *A61B 34/25* (2016.02); *A61B 34/30* (2016.02); *A61B 34/37* (2016.02);
(Continued)

(58) Field of Classification Search
None
See application file for complete search history.

(56) References Cited

U.S. PATENT DOCUMENTS

| 7,239,305 B1 * | 7/2007 | Nakano ................. G06F 3/0488 |
| | | 345/173 |
| 2005/0206753 A1 * | 9/2005 | Sakurai .................... G06T 3/00 |
| | | 348/241 |

(Continued)

FOREIGN PATENT DOCUMENTS

| JP | H05-337118 A | 12/1993 |
| JP | H08-280709 A | 10/1996 |

(Continued)

OTHER PUBLICATIONS

Jul. 7, 2016 Search Report issued in European Patent Application No. 13868654.8.
(Continued)

*Primary Examiner* — Erica S Lee
(74) *Attorney, Agent, or Firm* — Oliff PLC (57) ABSTRACT

A surgical robot which enables an operator to easily judge which medical instrument is selected is provided. This surgical robot has a robot body which selectively operates a plurality of medical instruments, an input unit configured to input control information of the robot body, the input unit being common among the plurality of medical instruments, and a display unit configured to display an image of a surgical site of a patient, the display unit having a selecting situation display function which displays a selecting situation of the plurality of medical instruments.

19 Claims, 9 Drawing Sheets

(51) Int. Cl.
*A61B 34/00* (2016.01)
*A61B 34/37* (2016.01)
*A61B 34/30* (2016.01)
*A61B 18/14* (2006.01)
*A61B 90/00* (2016.01)

(52) U.S. Cl.
CPC .......... *A61B 34/74* (2016.02); *A61B 18/1445* (2013.01); *A61B 90/361* (2016.02); *A61B 90/37* (2016.02); *A61B 2017/00464* (2013.01); *A61B 2017/00477* (2013.01); *A61B 2090/0811* (2016.02); *G05B 2219/39468* (2013.01); *G05B 2219/45117* (2013.01)

(56) References Cited

U.S. PATENT DOCUMENTS

| | | | | |
|---|---|---|---|---|
| 2006/0161789 | A1* | 7/2006 | Doughty | G06Q 20/327 |
| | | | | 713/186 |
| 2009/0192524 | A1* | 7/2009 | Itkowitz | A61B 90/37 |
| | | | | 606/130 |
| 2009/0326556 | A1* | 12/2009 | Diolaiti | A61B 1/00009 |
| | | | | 606/130 |
| 2010/0152614 | A1* | 6/2010 | Mark | A61B 17/32002 |
| | | | | 600/567 |
| 2010/0198402 | A1 | 8/2010 | Greer et al. | |
| 2010/0225209 | A1* | 9/2010 | Goldberg | A61B 34/30 |
| | | | | 312/209 |
| 2010/0228249 | A1 | 9/2010 | Mohr et al. | |
| 2011/0306986 | A1 | 12/2011 | Lee et al. | |
| 2013/0038707 | A1* | 2/2013 | Cunningham | H04N 7/183 |
| | | | | 348/65 |
| 2014/0157100 | A1* | 6/2014 | Evans | G06F 17/246 |
| | | | | 715/227 |

FOREIGN PATENT DOCUMENTS

| | | |
|---|---|---|
| JP | 2001-104333 A | 4/2001 |
| JP | 2002-253574 A | 9/2002 |
| WO | 2007/137304 A2 | 11/2007 |
| WO | 2011/116332 A2 | 9/2011 |

OTHER PUBLICATIONS

Mar. 4, 2014 International Search Report issued in International Patent Application No. PCT/JP2013/084647.

Jun. 30, 2015 International Preliminary Report on Patentability issued in International Patent Application No. PCT/JP2013/084647.

* cited by examiner

SURGICAL ROBOT

TECHNICAL FIELD

The present invention relates to a surgical robot for supporting a surgery using a plurality of medical instruments.

BACKGROUND ART

Conventionally, it is proposed that, in a surgical robot of a master/slave system, an image obtained from an endoscope related to a surgical site of a patient is presented to an operator (doctor), and a movement direction of a tip end of a medical instrument is composed so as to be presented to the same (Patent Document 1). Also, it is known that a plurality of medical instruments are operated by a common input portion of the surgical robot.

Conventionally, when a medical instrument to be operated is selected from a plurality of medical instruments so as to be operated by the common input portion of the surgical robot, operation directions of all medical instruments are displayed at the same time regardless of whether it is selected or not (Patent Document 1).

RELATED DOCUMENTS

Patent Document

[Patent Document 1] Japanese Patent Application Laid-Open No. 2001-104333

SUMMARY OF INVENTION

Problems to be Solved by the Invention

However, in the conventional surgical robot (Patent Document 1), an operator cannot easily judge which medical instrument has been selected and which switch of a plurality of switches or the like provided to the input portion of the surgical robot corresponds to which movement of the selected medical instrument.

The present invention has been made to deal with the above-mentioned problems of a conventional technique, aiming to provide a surgical robot capable of enabling an operator to easily judge which medical instrument has been selected.

Also, the present invention aims to provide a surgical robot capable of enabling an operator to easily judge which switch corresponds to which movement of a selected medical instrument.

Means for Solving the Problems

In order to solve the above-mentioned problems, a surgical robot of the present invention includes a robot body configured to selectively operate a plurality of medical instruments; an input unit configured to input a control information of the robot body, the input unit being common among the plurality of medical instruments; and a display unit configured to display an image of a surgical site of a patient, the display unit having a selecting situation display function which displays a selecting situation of the plurality of medical instruments.

Also, it is preferable that the selecting situation display function is to display on a screen of the display unit a mark and/or a letter for identifying the medical instrument which has been selected.

Also, it is preferable that the mark and/or letter is/are displayed so as to be overlapped at least partially on the medical instrument.

Also, it is preferable that the selecting situation display function is to erase a display of the selecting situation when a given time has passed after displaying the selecting situation of the plurality of medical instruments on a screen of the display unit.

Also, it is preferable that the display unit has a function which invalidates the selecting situation display unit.

Also, it is preferable that the input unit has a plurality of operation portions which correspond to a plurality of operation contents of the medical instruments, wherein the plurality of operation portions are provided with operated state detection units which are configured to detect operated states of respective operation portions, and wherein the display unit has an operation contents display function which displays an operation content of the medical instrument corresponding to the operation portion whose operated state has been detected by the operated state detection unit.

Also, it is preferable that the operation contents display function is to display a mark which is suggestive of the operation content.

Also, it is preferable that the mark which is suggestive of the operation content is displayed so as to be overlapped at least partially on the medical instrument.

Also, it is preferable that the operation contents display function erases a display of the operation content when a given time has passed after displaying the operation content on a screen of the display unit.

Also, it is preferable that the display unit has a function which invalidates the operation contents display function.

Also, it is preferable that the operated state detection unit is a contact and/or a proximity sensor.

Also, it is preferable that the operation portion has a first operation state and a second operation state that an operation progresses further from the first operation state, and wherein the operation contents display function is to display the operation content of the medical instrument in the first operation state.

Also, it is preferable that the operation portion includes a push-button type switch, and wherein the first operation state is a half-depressed state of the push-button type switch, and the second operation state is a state that the push-button type switch is depressed further from the half-depressed state.

Also, it is preferable that the display unit further has a switch display function which displays various switches, and wherein the input unit has an operation portion configured to actuate a desired switch among the various switches.

Also, it is preferable that the input unit comprises a plurality of input units, the display unit having a plurality of displays which correspond to the plurality of input units respectively.

Also, it is preferable that the input unit has a movable operation portion configured to move at least one of the plurality of medical instruments, and wherein the display unit sets a magnification of an operation amount of the medical instrument with respect to an operation amount of the movable operation portion to a reciprocal of a display magnification of the medical instrument.

Advantageous Effect of the Invention

The surgical robot of the present invention enables an operator to easily judge which medical instrument has been selected because a selecting situation on a plurality of medical instruments is displayed by a display unit for displaying an image of a surgical site of a patient.

BRIEF DESCRIPTION OF THE DRAWINGS

FIGS. 6A and 6B are schematic views illustrating a modified example of the surgical robot illustrated in FIG. 1; FIG. 6A illustrates a display example of a display, and FIG. 6B illustrates an operation panel of an input unit.

FIGS. 7A and 7B are schematic views illustrating another modified example of the surgical robot illustrated in FIG. 1; FIG. 7A illustrates a display example of a display, and FIG. 7B illustrates an operation panel of an input unit.

FIGS. 9A and 9B are schematic views for explaining a function of another modified example of the surgical robot illustrated in FIG. 2; FIG. 9A illustrates a screen when a display magnification is 1, and FIG. 9B illustrates a screen when a display magnification is 2.

EMBODIMENT OF THE INVENTION

Hereunder, the surgical robot according to an embodiment of the present invention will be described with reference to FIGS. 1 to 5.

Figure 1:
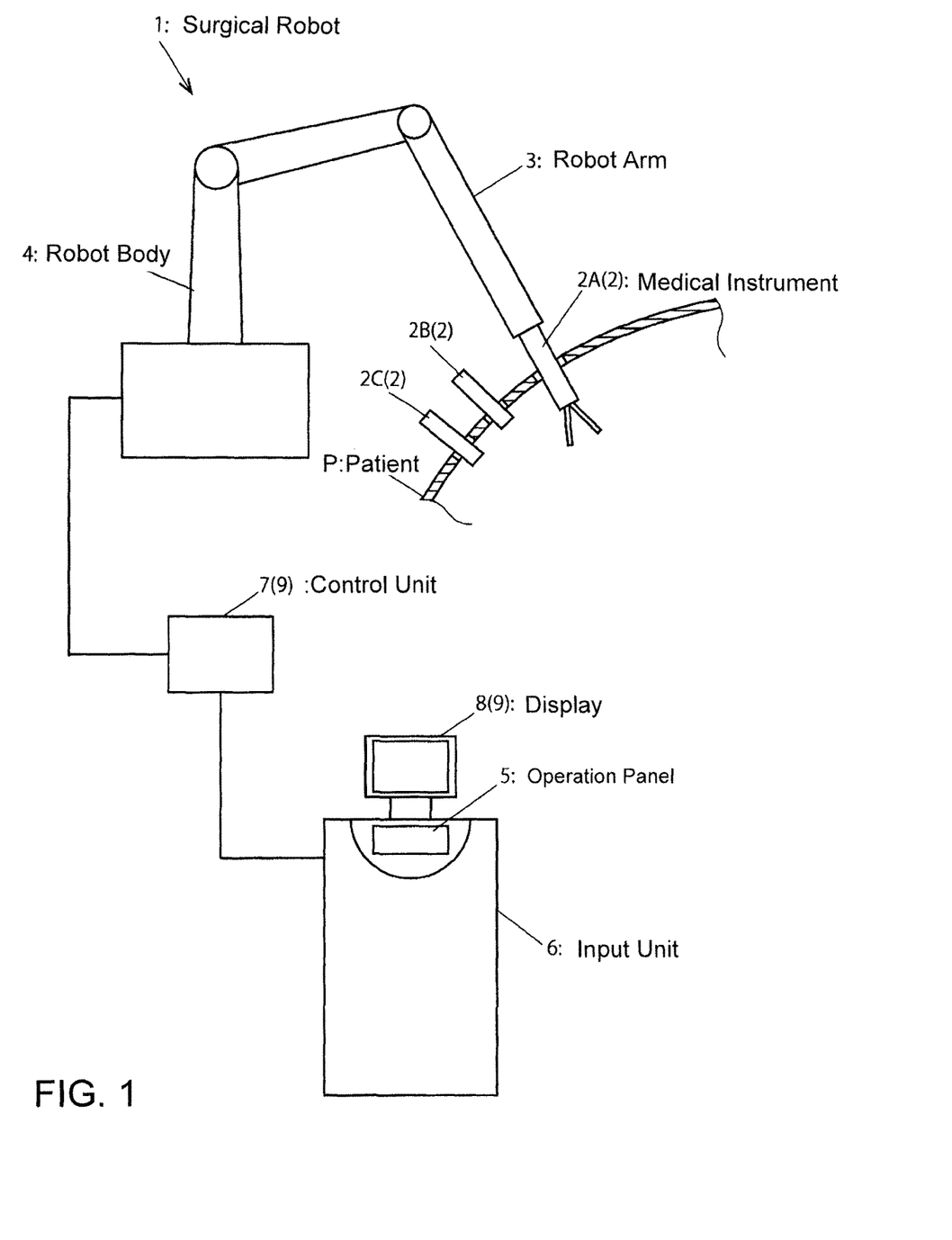
FIG. 1 is a schematic view illustrating an outline of a surgical robot according to an embodiment of the present invention.

As illustrated in FIG. 1, a surgical robot 1 of the present embodiment is provided with a robot body 4 having a robot arm 3 with a tip end to which a medical instrument 2 (2A, 2B, 2C) is mounted. Note that an illustration of the robot arm 3 to which the medical instruments 2B, 2C are mounted is omitted in FIG. 1. Control information of the robot body 4 is input to a control unit 7 by an input unit 6 which is provided with a control panel 5.

The control unit 7 controls the robot body 4 based on control information which is input from the input unit 6. The robot body 4 selectively operates a plurality of different kinds of medical instruments 2, and the common input unit 6 is used for a plurality of medical instruments 2. As the medical instrument 2, an instrument which clamps or cuts a surgical site or the like can be used, for example.

The surgical robot 1 further has an endoscope (not illustrated) for imaging a surgical site of a patient P, and a display 8 is installed adjacent to the operation panel 5 in order to present an image obtained from the endoscope to an operator.

An image of the display 8 is controlled by the control unit 7, and a display unit 9 in the surgical robot 1 of the present embodiment is configured by the display 8 and (a display control portion of) the control unit 7.

Figure 2A:
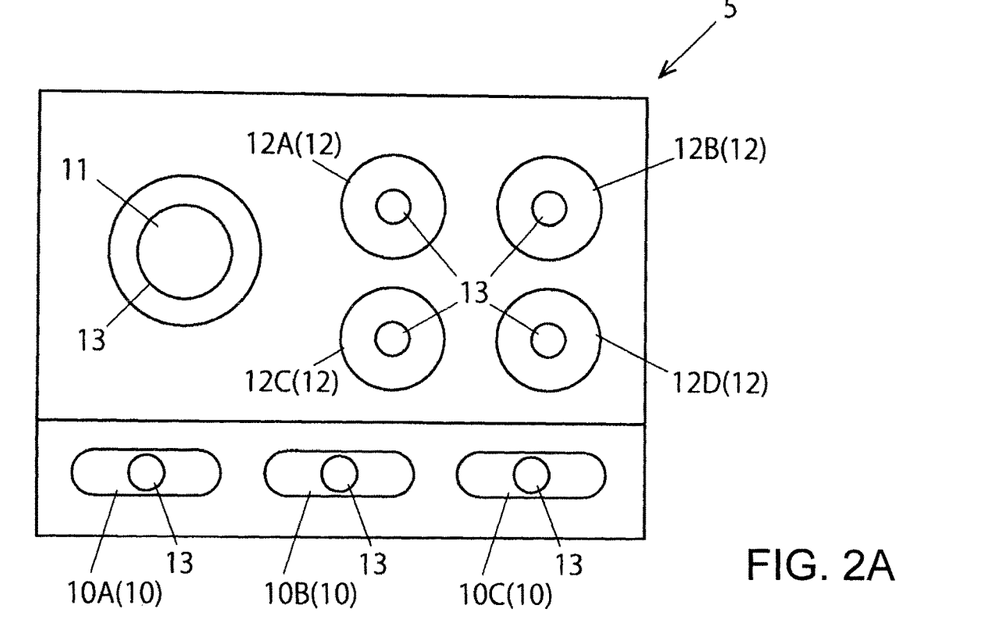
FIG. 2A is a plan view enlarging and schematically illustrating an operation panel of an input unit of the surgical robot illustrated in FIG. 1.
Figure 2B:
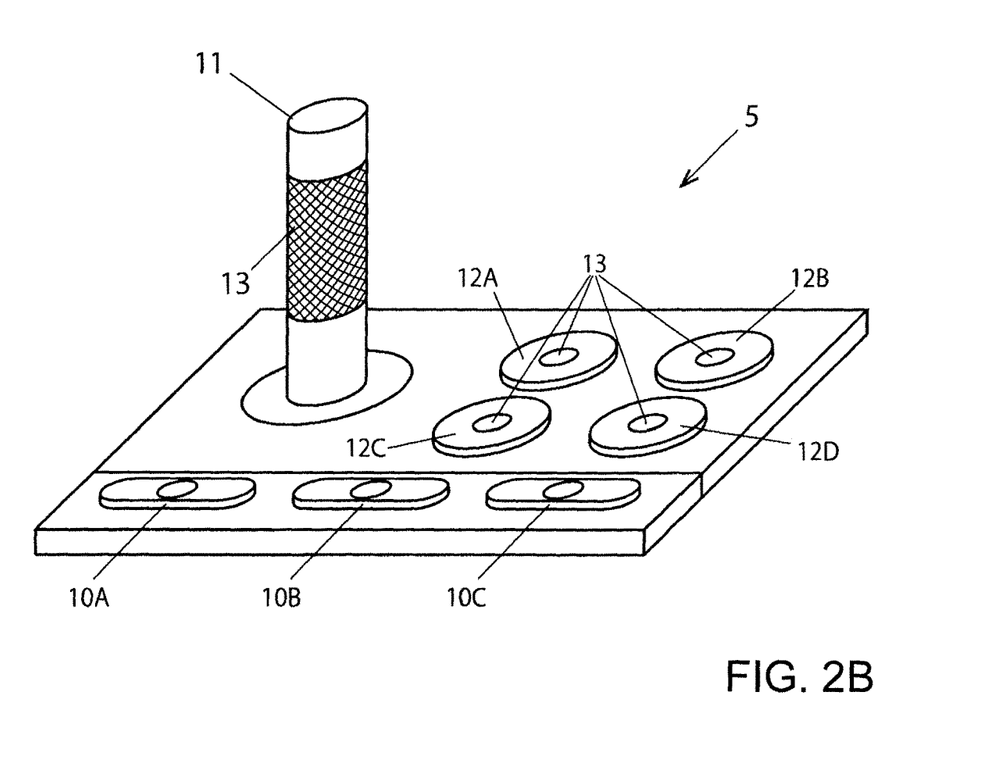
FIG. 2B is a perspective view enlarging and schematically illustrating the operation panel of the input unit of the surgical robot illustrated in FIG. 1.

In FIG. 2A and FIG. 2B, the operation panel 5 of the input unit 6 is displayed so as to be enlarged, and the operation panel 5 is provided with a selection switch (operation portion) 10 (10A, 10B, 10C) for selecting the medical instrument 2 to be used from a plurality of (three in the embodiment) medical instruments 2, a joystick (operation portion or movable operation portion) 11 for moving the selected medical instrument 2, and a startup switch (operation portion) 12 (12A, 12B, 12C, 12D) for performing various operations (four kinds in the example) by the selected medical instrument 2. The joystick 11 may be provided with the startup switch 12.

Each joint of the robot arm 3 is provided with a joint angle sensor (encoder, for example) for detecting a joint angle. Information of the joint angle sensor is transmitted to the control unit 7, and the control unit 7 recognizes the attitude of the robot arm 3 based on the transmitted information.

If a relative positional relation between each robot arm 3 on which each medical instrument 2 is mounted is known, the control unit 7 can recognize a relative positional relation of each medical instrument 2 and an endoscope by recognizing an attitude of each robot arm 3 as mentioned above.

The control unit 7 can recognize that the medical instruments 2A, 2B, 2C on the screen correspond to which of the selection switches 10A, 10B, 100 based on the relative positional relation of the respective medical instruments 2 and the endoscope which is recognized in this manner, and an image imaged by the endoscope.

Also, contact/proximity sensors (operated state detection units) 13 are provided to the joystick 11 and the startup switches 12 respectively. In addition to a mechanical sensor such as a switch or the like, various types of electric sensors including electrostatic capacitance type or the like can be used as the contact/proximity sensor 13. A detection signal of the contact/proximity sensor 13 is transmitted to the control unit 7, and thereby the operation portions 10, 11, 12 to be operated can be identified.

Figure 3:
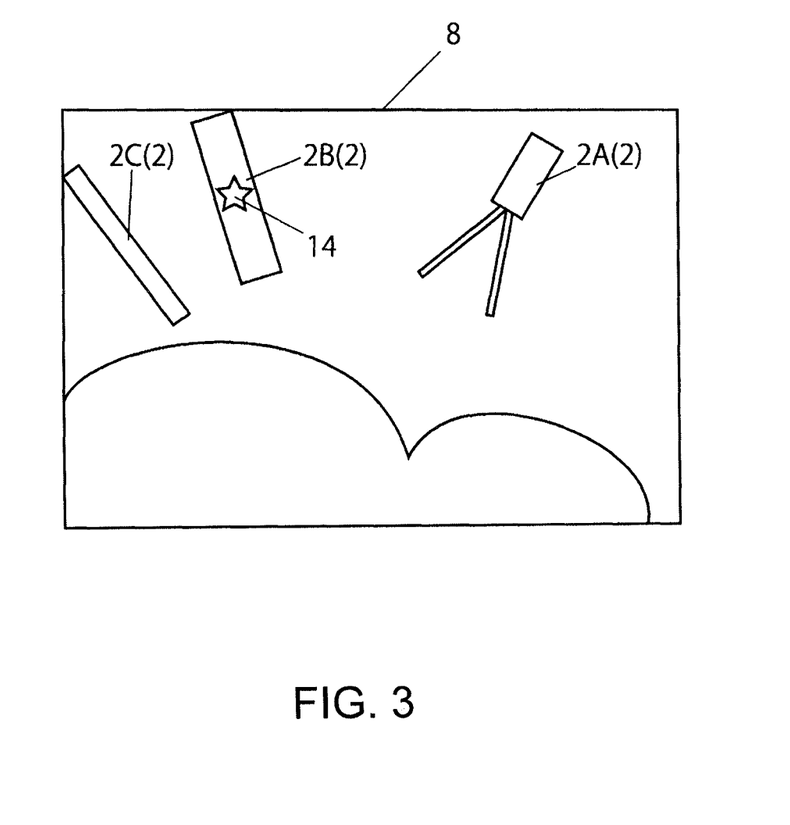
FIG. 3 is a schematic view illustrating a display example of a display of the surgical robot illustrated in FIG. 1.

FIG. 3 illustrates a display example of the display 8. The display unit 9 has a selected condition display function of displaying the selected condition of a plurality of medical instruments 2 on the screen. Also, the display unit 9 has a function of displaying moving directions and functions of the medical instruments 2 on the screen of the display 8.

In the example illustrated in FIG. 3, the selection switch 10B of the operation panel 5 is pressed so as to select the medical instrument 2B, and a star-shaped mark (mark) 14 is displayed in the Selected medical instrument 2B on the screen of the display 8.

Thus, as the selected medical instrument 2B can be confirmed with the mark 14 on the display 8, the operator can easily recognize the currently selected medical instrument 2B without taking his/her eyes off the display 8.

The mark 14 is displayed on the screen of the display 8 so as to be at least partially overlapped on the selected medical instrument 2B. Thereby, the selected medical instrument 2B can be easily recognized and also the mark 14 does not cut off a view, and therefore an image area of the display 8 can be used further efficiently.

Also, the mark 14 which indicates the selected medical instrument 2B can be constantly displayed on the display 8, while the mark 14 may be erased when a predetermined time has passed (after one second, for example) after the mark 14 has been once displayed. Thereby, the image area of the display 8 can be used further efficiently.

Also, the selected medical instrument 2B can be displayed on the screen of the display 8 with letters (letters such as "Electrosurgical Instrument", for example) as well as the display of the mark 14 which indicates the selected medical instrument 2B.

Also, the mark 14 may indicate the medical instrument 2B with an arrow in addition to a pattern such as a star-shaped mark as in the example. Namely, it would be sufficient for the way of display that the selected medical instrument 2B can be distinguished from the other medical instruments 2A, 2C. Note that, when two or more medical instruments 2 are selected at the same time, the mark 14 is attached to the respective medical instruments 2.

Also, the display unit 9 has a function of invalidating the selected condition display function. In some cases, the selected condition of the medical instrument 2 does not necessarily need to be displayed on the display 8 depending on the contents of a surgery performed and the type of the medical instrument 2 used. In such cases, the display function of the display 8 can be used effectively by preventing useless display on the display 8.

Also, the display unit 9 has an operation contents display function of displaying operation contents of the medical instruments 2 corresponding to the operation portions 11, 12 of which operated states are detected by the contact/proximity sensors 13 which are provided to the joystick 11 and the startup switch 12.

Figure 4:
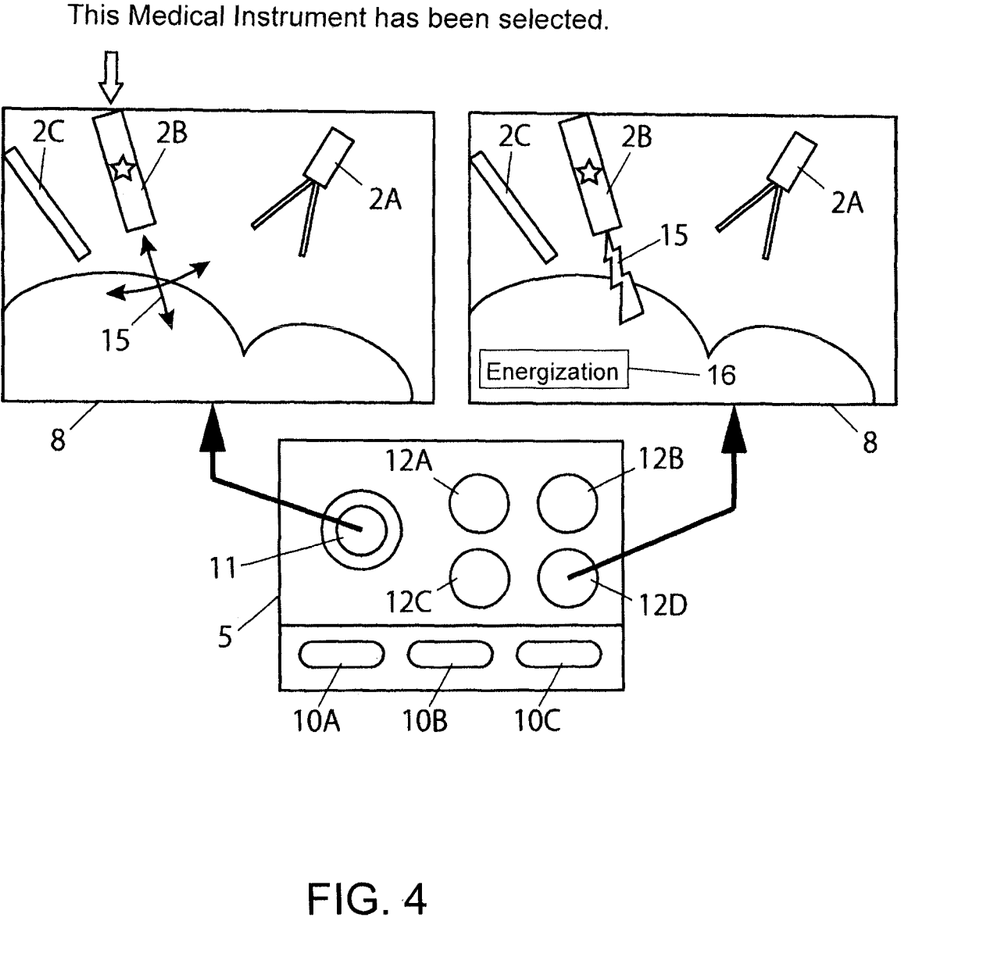
FIG. 4 is a schematic view for explaining a function of the surgical robot illustrated in FIG. 1.

The screen of the display 8 on the left side in FIG. 4 displays a mark 15 adjacent to the selected medical instrument 2B and suggestive of operation contents (moving direction in this case) when an operator holds the joystick 11 in the state that the selection switch 10B is pressed so as to select the medical instrument 2B.

On the other hand, the screen of the display 8 on the right side in FIG. 4 displays the mark 15 adjacent to the selected medical instrument 2B and suggestive of operation contents (energization to the electrosurgical instrument in this case) when an operator makes contact with the startup switch 12D in the same state that the medical instrument 2B is selected.

Note that, on the screen of the display 8, the mark 15 suggestive of operation contents can be displayed so as to be at least partially overlapped on the medical instrument 2. Thereby, an operator can easily recognize operation contents of the medical instrument 2 and also the image area of the display 8 can be efficiently used as the mark 15 does not cut off a view.

Also, operation contents can be displayed on the screen of the display 8 with a letter 16 ("Energization", for example) as well as display of the mark 15 suggestive of operation contents.

Also, the mark 15 and the letter 16 indicating operation contents of the medical instrument 2 can be constantly displayed on the display 8, while the mark 15 and a letter 16 may be erased when a predetermined time has passed (after one second, for example) after mark 15 and a letter 16 have been displayed. Thereby, the image area of the display 8 can be used further efficiently.

Also, the display unit 8 has a function of invalidating the operation contents display function. In some cases, operation contents of the medical instrument 2 do not necessarily need to be displayed on the display 8 depending on the contents of a surgery performed and the type of the medical instrument 2 used. In such cases, the display function of the display 8 can be used effectively by preventing useless display on the display 8.

Figure 5:
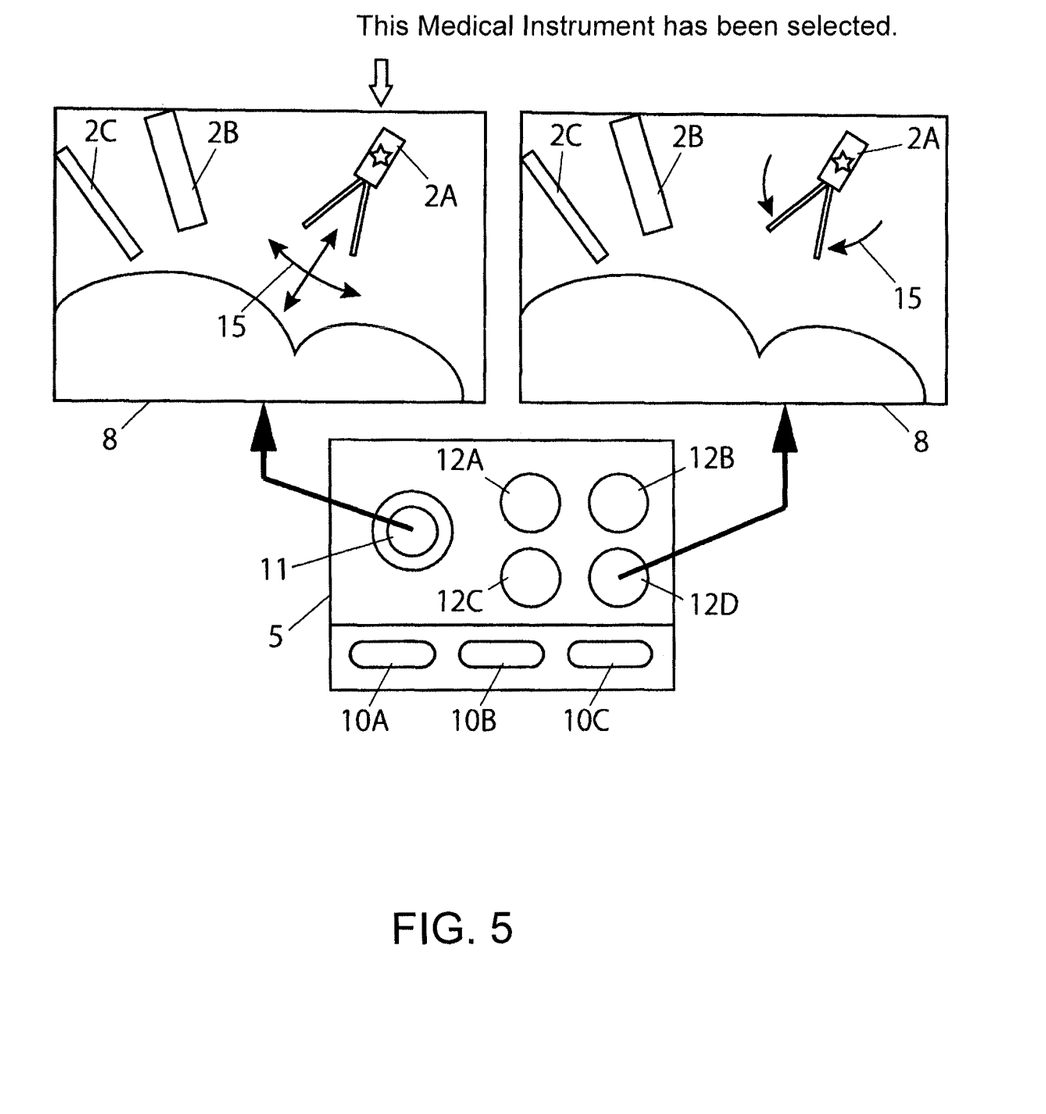
FIG. 5 a schematic view for explaining a function of the surgical robot illustrated in FIG. 1.

The screen of the display 8 on the left side in FIG. 5 displays the mark 15 adjacent to the selected medical instrument 2A and suggestive of operation contents (moving direction in this case) when an operator holds the joystick 11 in the state that the selection switch 10A is pressed so as to select the medical instrument 2A.

On the other hand, the screen of the display 8 on the right side in FIG. 5 displays the mark 15 adjacent to the selected medical instrument 2A and suggestive of operation contents (operation of closing a forceps in this case) when an operator makes contact with the startup switch 12D in the same state that the medical instrument 2A is selected.

As can be seen from FIG. 4 and FIG. 5, in the surgical robot 1 of the embodiment, different medical instruments (medical instruments 2A, 2B, for example) can be operated with the common startup switch (startup switch 12D, for example), and therefore the number of the startup switches 12 to be installed can be decreased.

Additionally, as operation contents are displayed on the screen of the display 8 according to the selected medical instrument 2, an operator can recognize the operation contents easily even when different medical instruments 2 are operated by the common startup switch 12.

As a modified example of the surgical robot 1 according to the above-described embodiment, the operation portion such as the startup switch 12 can be configured by a switch which has a first operation state and a second operation state that an operation further progresses from the first operation state, and also the operation contents display function displays operation contents of the medical instrument 2 in the first operation state.

For example, when the operation portion such as the startup switch 12 is configured by a push-button type switch, the first operation state is a half-depressed state of the push-button type switch, and the second operation state is a state that the push-button type switch is depressed further from the half-depressed state.

In the modified example, at the time when the operation portion (push-button type switch, for example) reaches the second operation state (state of being depressed further from the half-depressed state), the corresponding medical instrument 2 performs a predetermined operation (energization to the electrosurgical instrument, for example).

As another modified example of the surgical robot 1 according to the above-described embodiment, voice guidance can be used together with the marks 14, 15 and the letter 16 by the display unit 9.

Also, as the operation portions 10, 11, 12, a passive arm with multiple degrees of freedom and a grip or the like which detects gripping amount may be used in addition to the above-mentioned switch and joystick.

As another modified example of the surgical robot 1 according to the above-described embodiment, the display unit 9 may further have a switch display function of displaying various switches other than the joystick 11 on the display 8 so as to operate the switches by movements of a pointer (cursor) on the display 8 and clicks.

Figure 6A:
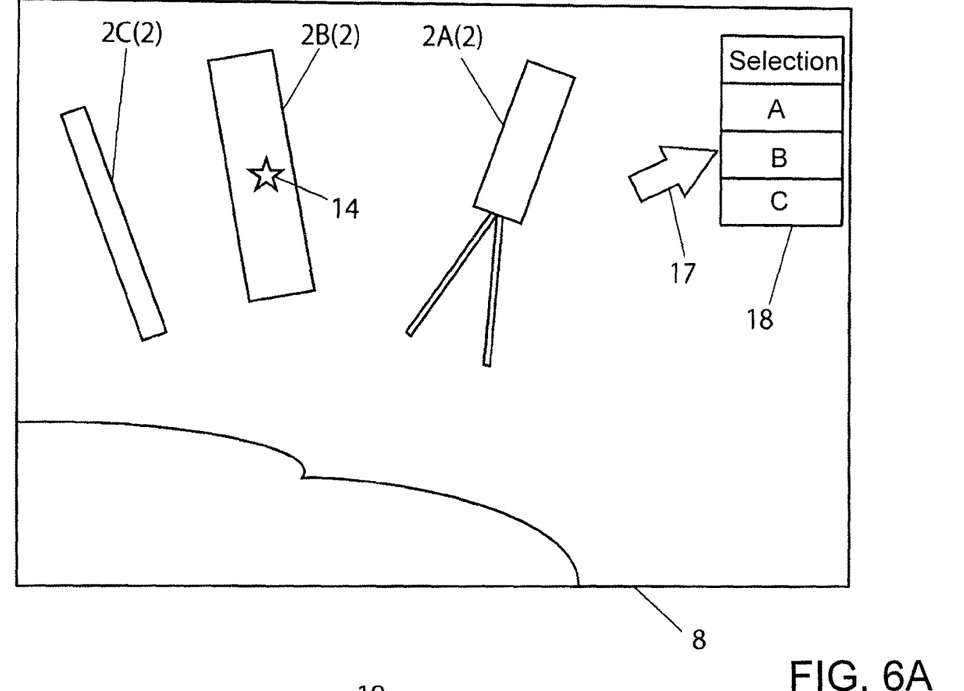
Figure 6B:
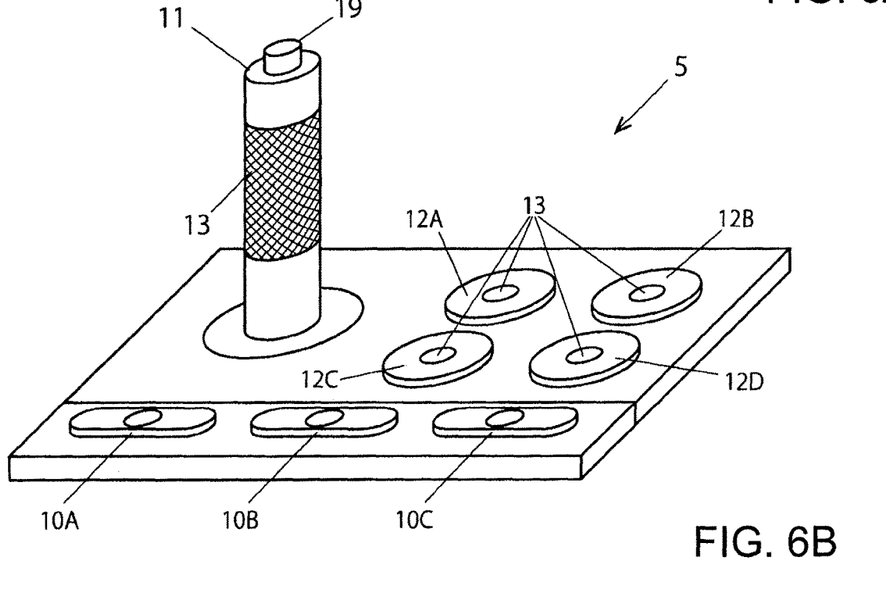

For example, as illustrated in FIGS. 6A and 6B, a pointer 17 displayed on the display 8 is moved by the joystick 11 so as to move the pointer 17 to the position of a desired switch of a slave screen 18 displayed similarly on the display 8. Here, in the example illustrated in FIG. 6A, the slave screen 18 configures a selection switch for selecting various medical instruments 2A, 2B, 2C.

Once the pointer 17 is moved to the position of the desired selection switch ("Instrument B" in FIG. 6A) of the slave screen 18 by operating the joystick 11, an operation button 19 provided to an end portion of the joystick 11 is pressed so as to select a desired medical instrument.

Thereby, since the star-shaped mark (mark) 14 is displayed in the selected medical instrument 2B as illustrated in FIG. 6A, an operator can easily recognize the currently selected medical instrument 2B without taking his/her eyes of the operator off the display 8.

Additionally, in the modified example, an operation itself for selecting the desired medical instrument 2 can be also performed without taking his/her eyes of the operator off the display 8. Also, the selection switches 10A, 10B, 100 of the operation panel 5 can be omitted.

Also, the operation button 19 provided to the end portion of the joystick 11 may be used as a startup switch for starting up the selected medical instrument 2B.

In this manner, an operator can start up the desired medical instrument 2B without taking his/her eyes of the operator off the display 8. Also, the startup switches 12A, 12B, 12C, 12D of the operation panel 5 can be omitted.

Figure 7A:
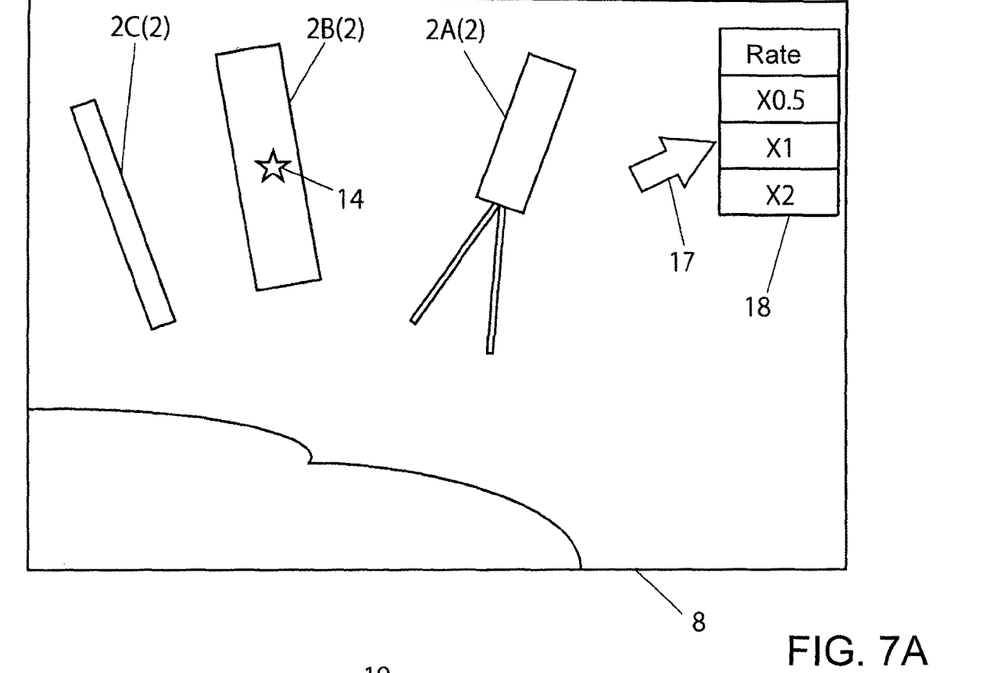
Figure 7B:
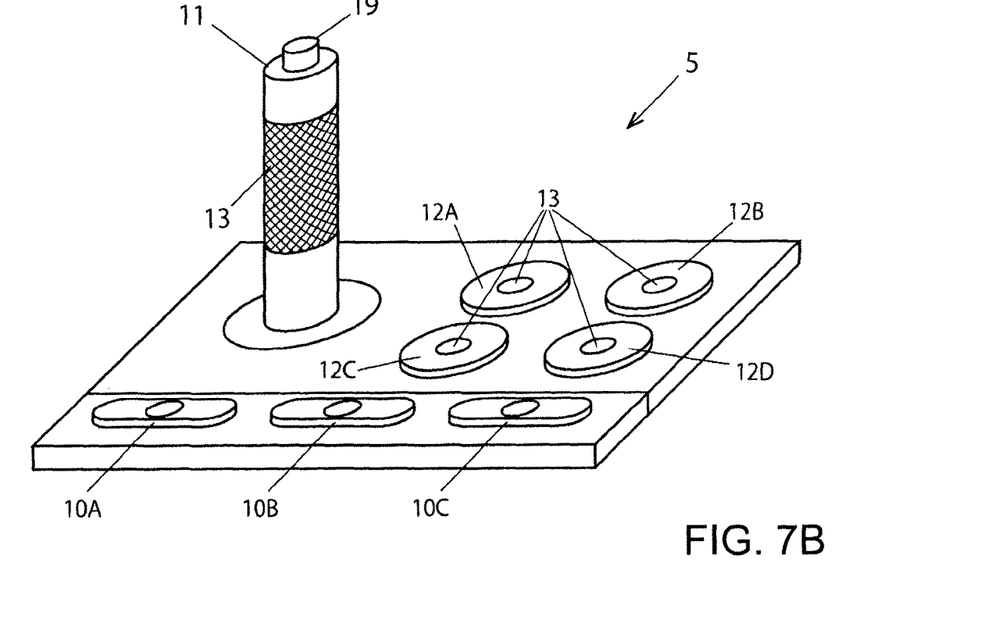

FIGS. 7A and 7B illustrates another modified example, and when the pointer 17 is positioned on the switch of the slave screen 18 displayed on the display 8, the medical instrument 2 concerned with the switch is specified in this modified example.

For example, when the pointer 17 is positioned to a switch "×2" as illustrated in FIG. 7A, the star-shaped mark (mark) 14 is displayed in a medical instrument (medical instrument 2B in FIG. 7A) whose magnification rate becomes 2 times thereby. Here, the "magnification rate" is a magnification of operation amount of the medical instrument 2 or the like with respect to operation amount of the joystick (operation portion) 11.

Figure 8:
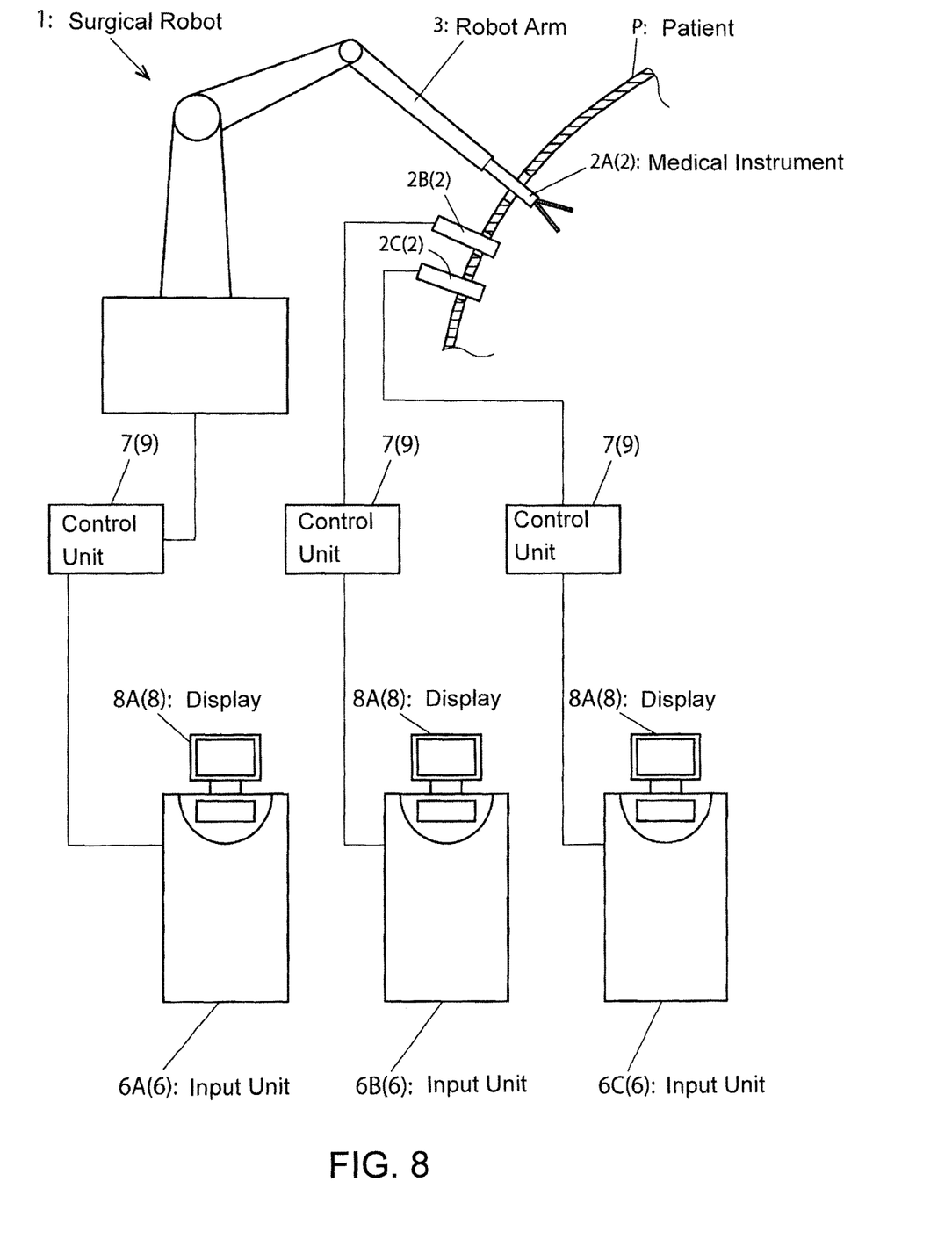
FIG. 8 is a schematic view illustrating another modified example of the surgical robot illustrated in FIG. 1.

FIG. 8 illustrates another modified example, and a plurality of input units (consoles) 6 are provided for one surgical robot 1 in this example. In this example, three input units 6A, 6B, 6C are installed.

Additionally, on the respective displays 8A, 8B, 8C of the plurality of input units 6A, 6B, 6C, common information to each other can be displayed. Therefore, operators can recognize via the displays 8 of their own that which switches of medical instruments 2 are being touched by other operators and which operation they are to perform.

According to the modified example, a plurality of operators can recognize each other's operation situation without taking their eyes off their displays upon co-operating, and therefore the co-operation can be performed smoothly.

Note that, although FIG. 8 illustrates an example that the displays 8 and the control units 7 are provided to the respective medical instruments 2, a common display or a control unit may be employed.

As another modified example, the above-mentioned magnification rate may be the reciprocal of the display magnification of the display 8.

Namely, this modified example enables an intuitive operation by maintaining operation amount of the medical instrument 2 on the display 8 with respect to certain operation amount of the joystick (operation portion) 11 regardless of display magnification.

Figure 9A:
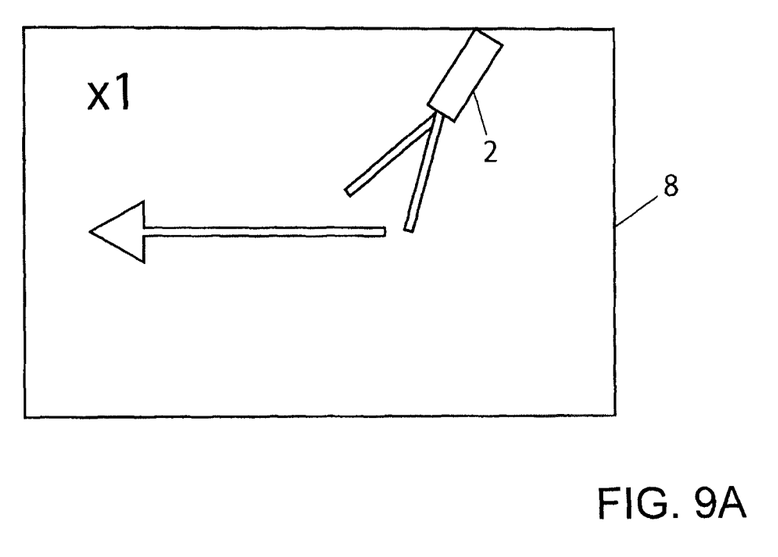

For example, operation amount of the medical instrument 2 on the display 8 when the joystick (operation portion) 11 is moved 1 cm to the left is shown by the length of an arrow illustrated in FIG. 9A.

Figure 9B:
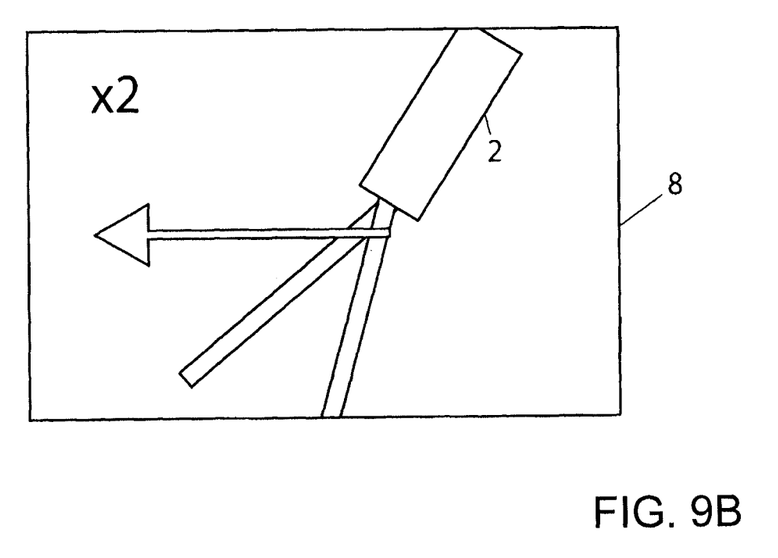

On the other hand, when the display magnification of the display 8 is increased to 2, operation amount of the medical instrument 2 with respect to operation amount of the joystick (operation portion) 11 is ½ as the reciprocal of 2. Thereby, operation amount of the medical instrument 2 on the display 8 when the operation portion 11 is moved 1 cm to the left is shown by an arrow in FIG. 9B, and it has the same length as the length of the arrow in FIG. 9A.

Namely, operation amount of the medical instrument 2 on the display 8 corresponding to a fixed operation amount of the joystick (operation amount) 11 is obtained by (display magnification of display)×(1/display magnification of display)=1 time, being constant regardless of magnification rate.

Thus, as a ratio of operation amount of the medical instrument 2 on the display 8 to operation amount of the joystick (operation portion) 11 is constant regardless of display magnification, an intuitive operation becomes possible.

Also, in such a case, a relation between a movable range of the joystick (operation portion) 11 and a display range of the display 8 also becomes constant, and thereby a movable range according to a display range and a display range according to a movable range can be set easily, which is advantageous on this point as well.

As described above, in the surgical robot 1 according to the embodiment and the modified examples thereof, the selected medical instrument 2 and the correspondence relation between the operation portions 11, 12 of the input unit 6 and the operation contents of the medical instrument 2 are displayed on the screen of the display 8, and thereby an operator can easily judge which medical instrument 2 is selected or which operation portions 11, 12 of the input unit 6 correspond to which operation of the medical instrument 2 via the screen of the display 8, namely, without taking his/her eyes off the display 8.

Note that the configuration of the present invention is not necessarily essential when the correspondence relation between the operation portions 11, 12 and the medical instrument 2 can be judged by a configuration or a method other than the present invention.

EXPLANATION OF REFERENCE NUMERALS

1 . . . surgical robot
2, 2A, 2B, 2C . . . medical instrument
3 . . . robot arm
4 . . . robot body
5 . . . operation panel
6, 6A, 6B, 6C . . . input unit
7 . . . control unit
8, 8A, 8B, 8C . . . display
9 . . . display unit
10(10A, 10B, 100) . . . selection switch (operation portion)
11 . . . joystick (operation portion or movable operation portion)
12(12A, 12B, 12C, 12D) . . . startup switch (operation portion)
13 . . . contact/proximity sensor (operated state detection unit)
14, 15 . . . mark
16 . . . letter
17 . . . pointer
18 . . . slave screen
19 . . . operation button
P . . . patient

The invention claimed is:

1. A surgical robot configured for use with a patient, the surgical robot comprising:
 a robot body configured to selectively operate a plurality of medical instruments;
 an input unit configured to input a control information for controlling at least one medical instrument, the input unit being operatively connected to the plurality of medical instruments, the input unit having a plurality of operation portions each corresponding to a plurality of operation contents of the respective medical instruments, and at least one of the plurality of the operation portions having: (a) a first operation state in which the operation portion is half-depressed by a manual operation, and (b) a second operation state in which the operation portion is fully depressed by the manual operation;

an operated state detection unit configured to detect whether the at least one of the operation portions are in the first operation state or the second operation state;

a display unit configured to display an image of a surgical site of the patient in real time, and to display an operation content of the medical instrument corresponding to the operation portion; and a common controller connected to the robot body, the input unit, and the display unit, the common controller being configured to:

recognize a plurality of medical instruments individually, determine, by the operated state detection unit, the operated state of the operation portion corresponding to the at least one medical instrument, display a mark and/or a letter superimposed over the real time image of the surgical site, the mark and/or the letter identifying the at least one medical instrument corresponding to the inputted control information, in response to determining that the operation portion corresponding to the at least one medical instrument is in the first operation state, display the operation content of the at least one medical instrument in the real time image, in response to determining that the operated state of the operation portion corresponding to the at least one medical instrument is in the second operation state, initiate an operation by the at least one medical instrument, and in response to a movement of the at least one medical instrument which is moved based on the control information in the real time image of the surgical site, change a location of the mark and/or the letter in the real time image.

2. The surgical robot according to claim 1, wherein the mark and/or letter is/are displayed so as to be overlapped at least partially on the medical instrument.

3. The surgical robot according to claim 1, wherein the display unit has a function that can be selected to disable the display of the mark and/or the letter.

4. The surgical robot according to claim 1, wherein the operation contents display function is to display a mark which is suggestive of the operation content.

5. The surgical robot according to claim 4, wherein the mark which is suggestive of the operation content is displayed so as to be overlapped at least partially on the medical instrument.

6. The surgical robot according to claim 1, wherein the operation contents display function erases a display of the operation content when a given time has passed after displaying the operation content on a screen of the display unit.

7. The surgical robot according to claim 1, wherein the display unit has a function which invalidates the operation contents display function.

8. The surgical robot according to claim 1, wherein the operated state detection unit is a contact and/or a proximity sensor.

9. The surgical robot according to claim 1, wherein the operation portion includes a push-button type switch, and wherein the first operation state is a half-depressed state of the push-button type switch, and the second operation state is a state that the push-button type switch is depressed further from the half-depressed state.

10. The surgical robot according to claim 1,
wherein the display unit further has a switch display function which displays various switches, and
wherein the input unit has an operation portion configured to actuate a desired switch among the various switches.

11. The surgical robot according to claim 1, wherein the input unit comprises a plurality of input units, the display unit having a plurality of displays which correspond to the plurality of input units respectively.

12. The surgical robot according to claim 1,
wherein the input unit has a movable operation portion configured to move at least one of the plurality of medical instruments, and
wherein the display unit sets a magnification of an operation amount of the medical instrument with respect to an operation amount of the movable operation portion to a reciprocal of a display magnification of the medical instrument.

13. The surgical robot according to claim 1, wherein the input unit has a plurality of operation portions.

14. The surgical robot according to claim 1, wherein the mark and/or the letter has a size such that the mark and/or letter could fit entirely within the at least one medical instrument when superimposed thereon.

15. The surgical robot according to claim 1, wherein
the mark and/or the letter is a rendered graphic image displayed together with the real time image of the surgical site, and
a location of the graphic image is changed in response to a movement of the at least one medical instrument.

16. The surgical robot according to claim 1, wherein the display unit includes a selecting situation display function which displays a selecting situation of the plurality of medical instruments displayed on the real time image of the surgical site.

17. The surgical robot according to claim 16, wherein the selecting situation display function is configured to erase a display of the mark and/or the letter when a given period of time has passed after displaying the mark and/or the letter on a screen of the display unit.

18. The surgical robot according to claim 1, wherein the display unit displays a different mark and/or letter for each controlled medical instrument.

19. A surgical robot configured for use with a patient, the surgical robot comprising:

a robot body configured to selectively operate a plurality of medical instruments;

an input unit configured to input a control information for controlling at least one medical instrument, the input unit being operatively connected to the plurality of medical instruments, the input unit having a plurality of operation portions each corresponding to a plurality of operation contents of the respective medical instruments, and at least one of the plurality of the operation portions having: (a) a first operation state in which the operation portion is half-depressed by a manual operation, and (b) a second operation state in which the operation portion is fully depressed by the manual operation;

an operated state detection unit configured to detect whether the at least one of the operation portions are in the first operation state or the second operation state;

a display unit configured to display an image of a surgical site of the patient in real time, and to display an operation content of the medical instrument corresponding to the operation portion; and a common controller connected to the robot body, the input unit, and the display unit, the common controller being configured to:

recognize a plurality of medical instruments individually, determine, by the operated state detection unit, the operated state of the operation portion corresponding to the at least one medical instrument, display a mark and/or a letter superimposed over the real time image of the surgical site, the mark and/or the letter identifying the at least one medical instrument corresponding to the inputted control information, in response to determining that the operation portion corresponding to the at least one medical instrument is in the first operation state, display the operation content of the at least one medical instrument in the real time image, in response to determining that the operated state of the operation portion corresponding to the at least one medical instrument is in the second operation state, initiate an operation by the at least one medical instrument, and in response to a movement of the at least one medical instrument which is moved based on the control information in the real time image of the surgical site, change a location of the mark and/or the letter in the real time image.

* * * * *